United States Patent
Pavesio et al.

(10) Patent No.: US 10,702,628 B2
(45) Date of Patent: Jul. 7, 2020

(54) HYALURONIC ACID DERIVATIVE AND NEURAL STEM CELLS FOR SCI AND PNT REGENERATION

(71) Applicant: ANIKA THERAPEUTICS S.R.L., Abano Terme (IT)

(72) Inventors: Alessandra Pavesio, Abano Terme (IT); Angelo Vescovi, Abano Terme (IT); Fabrizio Gelain, Abano Terme (IT); Maurizio Verga, Abano Terme (IT)

(73) Assignee: ANIKA THERAPEUTICS S.R.L., Abano Terme (IT)

( * ) Notice: Subject to any disclaimer, the term of this patent is extended or adjusted under 35 U.S.C. 154(b) by 0 days.

(21) Appl. No.: 15/668,716

(22) Filed: Aug. 4, 2017

(65) Prior Publication Data

US 2018/0140741 A1    May 24, 2018

Related U.S. Application Data

(63) Continuation of application No. 12/470,116, filed on May 21, 2009, now abandoned, which is a continuation of application No. 12/245,905, filed on Oct. 6, 2008, now abandoned, which is a continuation of application No. 11/795,428, filed as application No. PCT/EP2006/000398 on Jan. 18, 2006.

(60) Provisional application No. 60/644,587, filed on Jan. 19, 2005.

(51) Int. Cl.
*A61L 27/20*    (2006.01)
*A61L 27/38*    (2006.01)

(52) U.S. Cl.
CPC ............. *A61L 27/20* (2013.01); *A61L 27/383* (2013.01); *A61L 27/3878* (2013.01); *A61L 27/3895* (2013.01)

(58) Field of Classification Search
CPC .. A61L 27/20; A61L 27/3834; A61L 27/3878; A61L 27/3895; A61L 27/383
See application file for complete search history.

(56) References Cited

U.S. PATENT DOCUMENTS

| | | | | |
|---|---|---|---|---|
| 6,074,663 A | * | 6/2000 | Delmotte | A61L 15/32 424/422 |
| 6,482,231 B1 | | 11/2002 | Abatangelo et al. | |
| 6,830,927 B2 | * | 12/2004 | Rao | C12N 5/0623 435/368 |
| 2004/0037810 A1 | | 2/2004 | Heimburg et al. | |

FOREIGN PATENT DOCUMENTS

WO    WO-9958042 A2 * 11/1999 ............ A61K 35/30

OTHER PUBLICATIONS

Verdu et al. Alignment of collagen and laminin-containing gels improve nerve regeneration within silicone tubes. Restor Neurol Neurosci. 2002;20(5):169-79.*
"Neuroepithelial cell". Retrieved Jun. 6, 2019 from https://en.wikipedia.org/wiki/Neuroepithelial_cell.*
Grotta et al. (Eds.), Stroke: Pathophysiology, Diagnosis, and Management. 6th Edition. Elsevier. 2016.*
Cattaneo E. et al., "Proliferation and differentiation of neuronal stem cells regulated by nerve growth factor", Nature vol. 347, No. 6295, 1990, pp. 762-765.
Radice M. et al., "Hyaluronan-based biopolymers as delivery vehicles for bone-marrow-derived mesenchymal progenitors" Journal of Biomedical Material Research, May 2000, vol. 50, No. 2, pp. 101-109.
Seal B. et al., "Polymeric biomaterials for tissue and organ regeneration", Material Science and Engineering R; Reports Elsevier Sequoia S.A., Lausanne, CH, vol. 34, No. 4-5 Oct. 10, 2001, pp. 147-230.
Search Report and Written Opinion of PCT/EP2006/000398 dated Oct. 7, 2006.
Ramalho-Santos M., et al., ""Stemness": transcriptional profiling of embryonic and adult stem cells", Science, vol. 298, p. 597 (2002).
Yamada et al., "Vigorous neuronal differentiation of amplified and grafted basic fibroblast growth factor-responsive neurospheres derived from neuroepithelial stem cells", Cell Transplantation, vol. 13, pp. 421-428 (2004).

* cited by examiner

*Primary Examiner* — Gregory S Emch
(74) *Attorney, Agent, or Firm* — Silvia Salvadori, P.C.; Silvia Salvadori (57) ABSTRACT

A biomaterial for the treatment of spinal cord or of peripheral nerve injury, obtainable by:
  a) treating a hyaluronic acid derivative with a coating solution promoting Neuronal Stem Cells adhesion, branching and differentiation;
  b) contacting isolated Neuronal Stem Cells with the hyaluronic acid derivative obtained from step a) and culturing and expanding the absorbed cells in the presence of growth or neurotrophic factors selected from βFGF (basic fibroblast growth factor), CNTF (ciliary neurotrophic factor), BDNF (brain derived neurotrophic factor) and GDNF (glial derived neurotrophic factor) or mixtures thereof.

14 Claims, 10 Drawing Sheets

HYALURONIC ACID DERIVATIVE AND NEURAL STEM CELLS FOR SCI AND PNT REGENERATION

This non-provisional application is a continuation of U.S. application Ser. No. 12/470,116 filed May 21, 2009, which is a continuation of U.S. application Ser. No. 12/245,905 filed Oct. 6, 2008, which is a continuation of U.S. Ser. No. 11/795,428 filed Oct. 6, 2008 which is a National Stage Application of PCT/EP2006/000398 filed Jan. 18, 2006 which claims priority from and the benefit of the of U.S. Provisional Application No. 60/644,587 filed Jan. 19, 2005 the content of which are herein incorporated by reference in their entireties.

SUBJECT OF THE INVENTION

The present invention is directed to regeneration of Spinal Cord and Peripheral Nerve Injury after implantation of a scaffold made of a Hyaluronic acid derivative alone or in which Neural Stem cells are seeded.

BACKGROUND OF THE INVENTION

Hyaluronic acid is a major component of the extracellular matrix that surrounds migrating and proliferating cells. It is an extremely long, negatively charged polysaccharide, each molecule of which consists of as many as 50,000 replications of the simple disaccharide composed by Glucuronic acid and N-Acetylglucosamine. Indeed, it is important to mention successful in vivo applications of its derivatives in wound healing, diabetic ulcers, vitiligo treatments, laparoscopic adhesion prevention, anti-adhesive surface coatings, cartilage regeneration.

One class of HA derivatives are called auto-crosslinked polysaccharides. In this case the stability if the polymer was obtained by creating cross-linking bonds, but no additional chemicals were involved in bridging the hyaluronan chains. Stabilization was achieved by directly esterifying a certain percentage of the carboxyl groups of glucuronic acid along the polymeric chain with hydroxyl groups of the same or different hyaluronan molecules. These materials are highly viscous suspensions in sterile distilled water of auto-reticulate microparticles with variable concentrations of between 30 and 60 mg/mL.

An alternative way of obtaining HA derivatives involves the use of coupling reactions where specific functional groups of the polysaccharide (e.g. carboxyl, hydroxyl, N-acetyl groups) are modified by chemical reactions such as esterification, sulphatation, amidation and so on.

All of these HA modified biomaterials in vivo spontaneously degrade by enzymatic activity or hydrolysis, giving fragments of HA molecules and the functional groups previously bound (benzyl or ethyl alcohol, amides, etc.)

The synthesis of HA derivatives usually involves a two-step procedure: the preparation of a quaternary salt of HA and its subsequent reaction with a chemical agent (esterifying, amidating, etc) in aprotic solvent at a controlled temperature. A variety of alcohols can be used for esterification (aliphatic, araliphatic, cycloaliphatic and others). Amidated HA can be prepared according to EP 1095064. Hyaluronic acid esters are known for instance from EP 216453. O-sulphated derivatives of HA are known from EP 702699.

Percarboxylated derivatives of HA are known from EP 1339753.

According to the chemical group substituted during chemical reactions (and the percentage of substitution too) the resulting biomaterials could provide totally different mechanical properties: for example, in the case of esterified HA, the residence time increases by means of increased hydrophobicity and decreased negative charge of the carboxyl group.

Keratinocytes, fibroblasts, chondrocytes, mesenchymal stem cells, endothelial cells, hepatocytes, urethelial cells and nerve cells have proven to proliferate efficiently on HA modified biomaterials. However, the vast majority of the cross-linked HA derivatives previously mentioned are represented by very hydrated materials, which are not cell-adhesive and, for this reason, were initially considered as resorbable materials for the prevention of surgical adhesions.

Our first tissue engineering approach was to test this important variety of fully biodegradable biomaterials. HA-based products have received European Community approval for clinical applications, and three products have been FDA-approved.

SCI (Spinal Cord Injury) may be characterized as a result of continuing processes of tissue destruction, abortive repair, and wound healing around the injury site. A significant body of evidence suggests that SCI evolves through three phases: the acute, secondary, and chronic phase. The initial core lesion progressively expands and the SCI evolves into its chronic phase. White matter demonstrates partial or complete demyelinization that is responsible for conduction deficits. Approximately 25% of SCI patients develop a centrally located cyst that progressively expands leading to syringomyelia.

Further histopathologic features include gray matter dissolution, connective tissue deposition and gliosis. The range and location of injury determine the overall neurological deficit, development of hyperexcitability, and chronic pain syndromes.

If the main area of research interest is the physiologic response to injury or the pathophysiology of secondary injury, then the investigator might choose a contusion model, because it closely parallels human SCI. However, the unambiguous demonstration of regenerating axons in a contusion model poses a new challenge, specifically the delineation of spared and regenerated axons.

Behavioral studies and statistical evaluation of motor-sensory pathway recovery too could be an extremely critical step with contusion models, into which animal control groups (injured but not treated) spontaneously recover part of their lost nervous connectivity.

If a device is to be implemented, a partial or complete transection model might be best suited for device placement. For certain experimental paradigms, a combination of models might be planned. For example, the early stages of an experimental plan that explores axon regeneration might utilize transection models to demonstrate unambiguously regenerated axons and identify the most promising therapies, which can then be tested in contusion models by analysis techniques.

In a transection model the ability to differentiate spared axons from regenerated ones is not an issue. For certain applications, unilateral hemisection injury can be a viable alternative to complete transection. A major advantage of this approach is the preserved structural integrity and function of one side of the spinal cord. Unilateral spinal cord sparing is usually sufficient to maintain bladder and bowel function, which results in less-intensive post-operative animal care.

For these reasons, spinal cord hemisection in rats was used as an experimental animal model for testing spinal cord regeneration after injury and implantation of a scaffold made of esterified HA whereas, for testing peripheral nerve regeneration, a complete transection of the sciatic nerve has been carried out.

BRIEF DESCRIPTION OF THE DRAWINGS

FIGS. 2(a) and 2(b) show stained human neuronal cells seeded on microfibers.
FIGS. 2 (c) and 2(d) show a lamina of 100% esterified HA five days after plating.

DETAILED DESCRIPTION OF THE INVENTION

Hyaluronic-Acid-Derived Membranes and Fibers: A Multi-Component Scaffold

The first step of the experimentation of the invention was a broad, in vitro comparison between different versions of hyaluronic acid, partially and totally esterified, N-sulphated, partially amidated (gel), percarboxylated and some auto-crosslinked versions (gel). Particularly suitable for the invention herein described have proved to be the HA esters, and especially so the benzyl ester (HYAFF®11).

HA at different percentages of esterification (>70%, preferably from 75 to 100%, even more preferably 100% esterification degree) was provided in solid and partially flexible structures: ranging from non-woven meshes and parallel non-woven fibers to woven tubular structures and laminas already available from other studies and tissue engineering applications as skin, vascular tissue, cartilage regeneration. All of the in vitro screening experiments were done following the protocols established for harvesting and expanding NSCs (Neural Stem Cells).

The experimental protocol is described below:
only similar 3-dimensional scaffolds were compared (i.e. fibers with fibers, laminas with laminas);
mechanical dissociation of neural stem cells two days before seeding to keep the percentage of stem cells over the mixed cell population as high as possible;
in some cases, HA scaffolds were submerged into different coating solutions: mouse laminin (5 μg/cm$^2$), human fibronectin (10 μg/cm$^2$), laminin and fibronectin mixed;
200,000-300,000 total numbers of cells seeded per condition, concentrated in 20 μl of medium;
each scaffold was soaked for 30 min with only this highly concentrated cell solution;
addition of a medium containing bFGF at a final concentration of 20 ng/ml;
after 3 days, the medium was shifted to a CNTF and BDNF composed medium (20 ng/ml in both cases);
medium replacement every 2 days;
cell viability tested 7 and 14 days after plating by MTT assay;
in cases of cell survival, a staining imaging by confocal and fluorescence inverted microscopes was conducted;
mouse and human neural stem cells were used.

Figure 1:
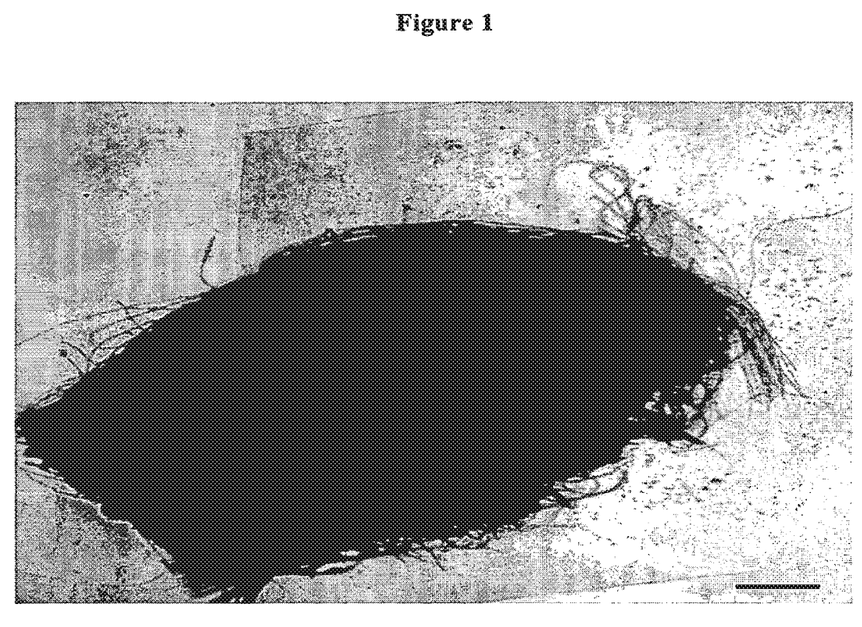
FIG. 1 shows a rope and lamina of esterified HA.

In FIG. 1 it is clearly visible the blue color of a rope of non-woven fibers and a lamina made of totally esterified HA given by the living cells MTT staining.

The blue colour is due to the production by living mitochondria of insoluble blue formazans products with the MTT reagent. The fibers are entirely covered with living cells. Scale bar is 500 μm.

Of the coating solutions tested, fibronectin and laminin mixed together showed the highest cell survival rate: this comparison was conducted for all of the biomaterials previously mentioned keeping the same cell culture medium. Consequently, this coating solution was adopted from this time point as part of our standard protocol for all of the successive in vitro and in vivo experiments.

As the next step, we tested different combination growth and neurotrophic factors diluted in the culture medium in order to favor NSC proliferation, differentiation toward the neuronal phenotype and to choose proteins that had been proved to enhance nervous system regeneration in in vivo experiments.

We therefore tested the effect on cell proliferation of:
βFGF (basic fibroblast growth factor)
βFGF+CNTF (ciliary neurotrophic factor)
βFGF+CNTF+BDNF (brain derived neurotrophic factor)
βFGF+CNTF+BDNF+GDNF (glial derived neurotrophic factor)

All of these last mentioned growth factors were tested in a 20 ng/ml concentration.

In table 1 it is clearly seen the highest value of absorbance (living NSCs) obtained for the most complete combination of neurotrophic factors, both for non-woven fibers and lamina scaffolds.

TABLE 1

MTT assay for mouse NSCs seeded on fibers and on lamina made scaffold of 100% esterified HA, 7 days after plating.

| 100% esterified HA | βFGF | βFGF + CNTF | βFGF + CNTF + BDNF | βFGF + CNTF + BDNF + GDNF |
|---|---|---|---|---|
| lamina | 0.09 ± 0.01 | 0.123 ± 0.013 | 0.2 ± 0.032 | 0.252 ± 0.044 |

TABLE 1-continued

MTT assay for mouse NSCs seeded on fibers and on lamina made scaffold of 100% esterified HA, 7 days after plating.

| 100% esterified HA | βFGF | βFGF + CNTF | βFGF + CNTF + BDNF | βFGF + CNTF + BDNF + GDNF |
|---|---|---|---|---|
| fibers | 1.32 ± 0.101 | 1.88 ± 0.162 | 2.053 ± 0.169 | 2.4683 ± 0.369 |

The trophic factor included in the medium strongly influenced the final size of the living cell population (n=8). Values are expressed in Absorbance Units. All of these trends in MTT assays were reproduced using human NSCs too.

Cell morphology and topographical distribution on lamina and fiber scaffolds was evaluated by upright and inverted light microscopes for all the experiments previously described, both for mouse and human cells.

Figure 2:
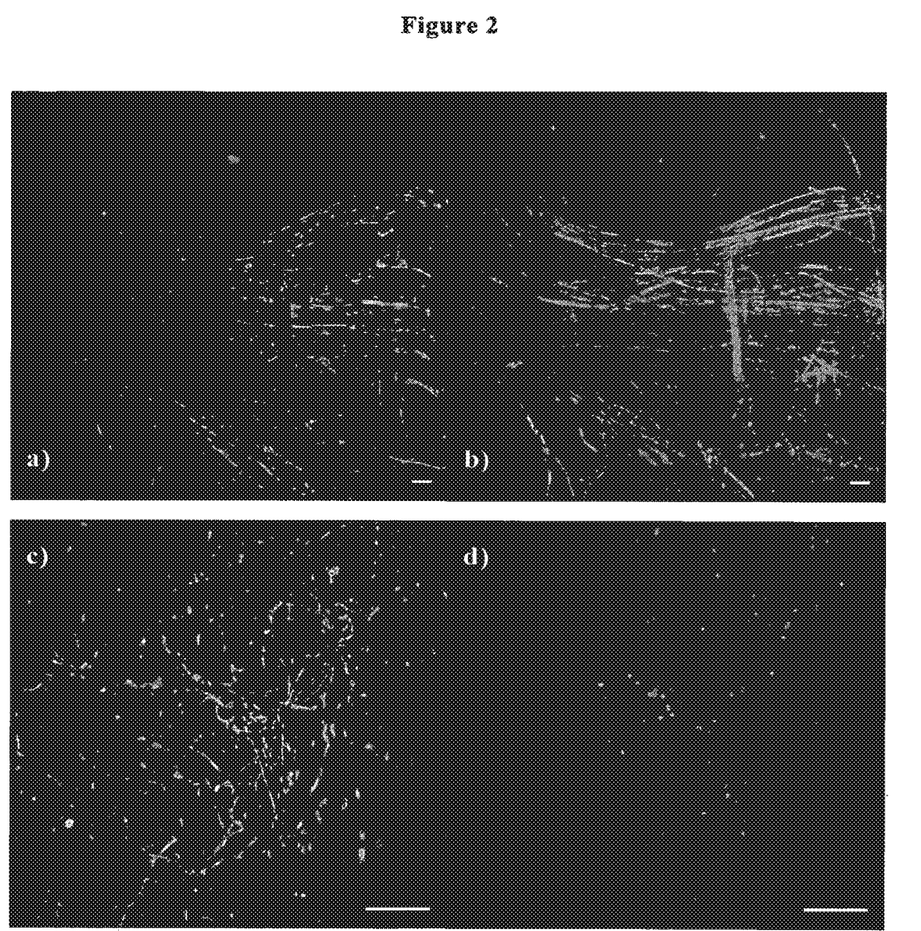

FIG. 2 shows staining of human neural stem cells seeded on microfibers (a,b) and a lamina (c,d) of 100% esterified HA 5 days after plating. Cell nuclei (b,d) are stained blue with DAPI. In the left column, neurons and astrocytes are stained in green with B Tubulin antibody (a,c,) and in red with GFAP antibody (c only). In the case of fibers, it is possible to note how differentiating NSCs elongate their bodies and extend their branches following the longitudinal axes of each fiber. Scale bars are 50 μm.

Fluorescent labeling too proved essential for testing cell morphology in 3-dimensional scaffolds: in this case imaging was conducted by fluorescence and confocal fluorescence microscopy.

A sufficiently uniform cell distribution was reached for non-woven fibers and lamina scaffolds: non-woven meshes and woven tubes proved difficult to be uniformly seeded in static conditions (i.e. with cells and scaffolds not exposed to any artificial medium flow).

By the end of our in vitro experimentation it has been possible to almost completely cover the HA fibers with adhering NSCs. To do so, growth factors were used to stimulate cells proliferation and spontaneously migration between fibers.

Confocal microscopy proved to be an essential technique for cell-scaffold three-dimensional imaging and cell counting on account of its high-resolution scanning.

We also tested gel bioscaffolds made of auto-crosslinked HA (projected for anti-adhesive applications), amidated HA and HA with 65% and 50% esterification: all of these were in powder form and were tested at different dilutions in distilled water.

The preferred conditions involved mixing the dried powder of the auto-crosslinked HA with the medium (containing bFGF, CNTF, BDNF, GDNF) and a coating solution (preferably comprising fibronectin and laminin) as disclosed above; remarkable cell adhesions and branching (see FIG. 3) and the beginning of in vitro cell network formation have been obtained using these conditions.

Figure 3:
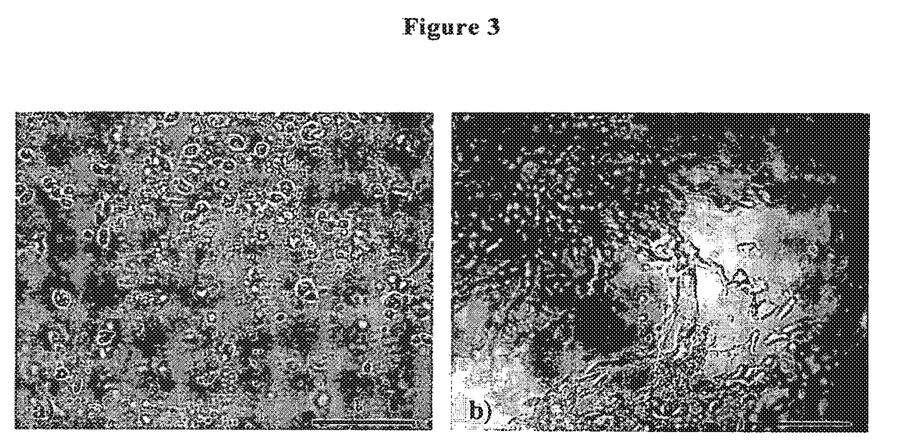
FIG. 3 shows phase contrast light imaging of NSCs seeded into auto-crosslinked HA gels 4 days after plating.

In particular, FIG. 3 shows phase contrast light imaging of NSCs seeded into auto-crosslinked HA gels 4 days after plating. In figure (a) the HA was diluted in distilled water, in (b) HA was diluted in our abovementioned differentiating medium and coating solution made of laminin and fibronectin. The round shaped cells shown in (a) indicate total absence of cell adhesion, branching and differentiation, this usually will lead to cell apoptosis or senescence; on the other hand, the branched cells shown in (b) provide a clue to a more favorable environment for NSCs differentiation and survival. Scale bars are 50 μm.

Animal Models and Scaffold Design

For the reasons described above, a spinal cord hemisection in rats was used as experimental animal model for testing spinal cord regeneration after injury and implantation of a scaffold made of HYAFF®11.

In order to ensure the reliability of the results in peripheral nerve injury experiments, a complete transection of the sciatic nerve in rats was carried out. For both SCI and PNT (Peripheral Nerve Transection) three different animal groups were created: rats with lesions only (control group), rats with lesions and transplanted with human (and sometimes mouse) NSCs differentiated on biopolymeric matrices, and rats receiving scaffolds alone.

In an attempt to induce a 3D oriented cell growth and differentiation, we designed and tested similar scaffolds for both SCI and PNT:

100% HA benzyl ester was selected as the main component of the scaffolds because of the promising results obtained in in vitro experiments (see previous chapter) and the estimated biodegradation time (2-3 months) which was close to the desired goal.

simplifying the cytoarchitecture of most of the spinal cord tract and peripheral nerves to longitudinally oriented nervous fibers, we adopted fibers (20 μm-50 μm) spatially oriented as 3D supports able to influence cell orientation (demonstrated in the previous chapter) and correct spatial endogenous neurite regeneration.

Because of its intrinsically open, porous structure and poor mechanical stiffness, in the case of PNT these fiber-made matrices were inserted in tubes (made of the same biomaterial) 2 mm wide having either continuous or porous walls. Said tubes may be subjected to laser puncture so as to allow the penetration of the glia within the tube, releasing the growth factors making nerve regeneration easier. Small tubes consisting of HYAFF®11 fibers are already known and have been used for example for the regeneration of urethra (Italiano G. et al., *Urol Res*, 1997, 26:281-284). EP 571415 discloses a cylinder of HYAFF®11 supported by a helicoidal wire always consisting of HA and enriched with growth factors. EP 652778 discloses a network of several woven wires supporting the HA tube, said wires consisting of the same materials and inserted into the tube body, in order to make them more compact; also in this case, a growth factor is present. These known scaffolds, even though developed for the generation of nervous fibers, have important drawbacks as to the elasticity in following the complex regenerative process of the peripheral nerve, in view of the lack of flexibility and adaptable to the nerve path.

For the SCI model, the fiber scaffold was first placed in the injury site, then a square lamina was used as patch to isolate the regeneration site from the harmful invasion of connective and muscular cells from tissues surrounding the injury. In the case of PNT, the tubes were sutured to the nerve stumps, for SCI the patches were sealed by fibrin glue (a biological paste commonly used in clinical surgery).

Figure 4:
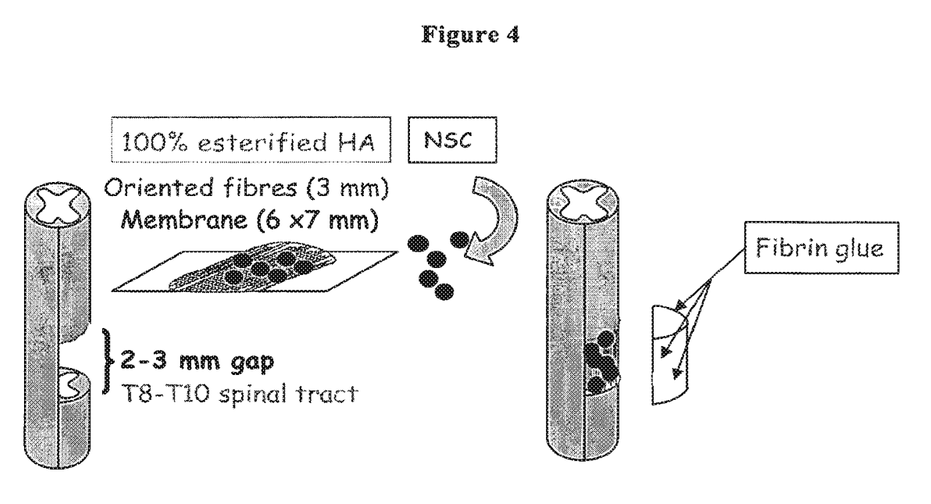
FIG. 4 depicts a schematic representation of surgery for SCI.

A schematic representation of the surgery for SCI is shown in FIG. 4. The main differences from the PNT model are the site of injury (sciatic nerve), the length of the nervous gap (1 mm), the external scaffold component (a tube instead of a lamina) and the use of suture instead of fibrin glue to stick the transplant to the host tissue.

NSCs were seeded on an HA scaffold and cultured for 2 days in vitro. Immediately after spinal cord injury made by incision, cells and fibers were placed along the longitudinal axis of the spinal tracts. Then fibrin glue was used to seal the HA membrane.

The detailed protocol makes use of our first in vitro experimentation about culture medium and coating:
- neurospheres (or clusters of NSCs) were mechanically dissociated 2 days before seeding;
- the day before cell seeding, each component of the scaffold was submerged in a coating solution made of laminin (25 µg/ml) and fibronectin (50 µg/ml) and left overnight;
- $5 \times 10^5$-$7.5 \times 10^5$ NSCs were resuspended in 20 µl of culture medium. The cell suspension was poured on the scaffolds and left for 30' at 37° C.+ as a pre-adhesion step;
- seeded cells were then cultured for two days in vitro with medium containing βFGF, CNTF, GDNF, BDNF.

Biopolymer+cells were inserted in the acute lesion in the spinal cord (hemisection and tissue removal of 3 mm half portion of T9 spinal tract) of adult Sprague-Dawley female rats (250 gr) and sealed with fibrin glue.

Control animals received the scaffold without cells or only underwent lesion. After surgery, the animals received daily doses of cyclosporine as immuno suppressor.

The animals were monitored twice a week to evaluate the entity of functional damage and were scarified 1-2 or 6 months after transplantation.

After intracardiac perfusion of PFA 4%, the spinal was removed and processed for histochemical analysis.

In PNT models, a complete transection of the sciatic nerve was executed, a 1 mm long strip of nervous tissue was removed, and a bridge made of cells and scaffold (fibers and tube) was sutured to both stumps. In this case too, animal control groups were used (scaffold without cells, surgery without any treatment).

In Vivo Application of HYAFF®11-Based Scaffolds: Results

For the SCI model, over 40 animals were used: on each day of surgery, at least one animal from each group was operated on. Animals were sacrificed and spinal cord tissue was embedded in PFA 4% and cryo-sectioned into coronal and longitudinal sections. Then morphological and immunohistochemical analyses were conducted.

To prevent an unwanted immune response to transplanted cells, the animals received daily doses of cyclosporine till the day of their sacrifice.

Different cell lines were used for transplantations: human neural stem cells, mouse NSCs, transgenic mouse NSCs (modified to express a marker inside their nuclei, β-Galactosidase, to allow their localization in cryo-sections of the host tissue).

Figure 5:
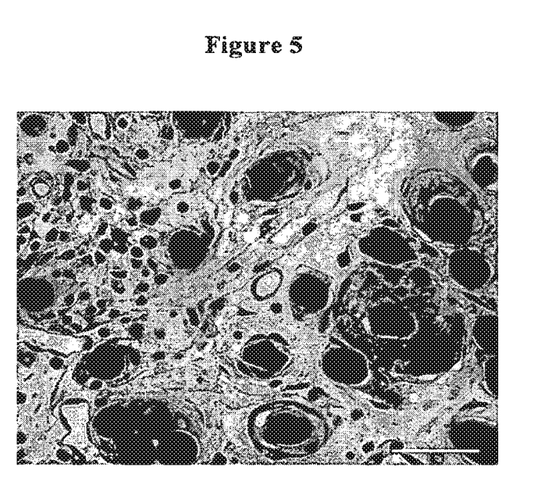
FIG. 5 shows Blue Toluidine staining for acid components included in a coronal section of cells and scanhold three weeks after treatment.

In the early weeks after transplantation, an ordinary (for a physiological follow up of SCI) invasion of monocytes, T-cells and other immune response related cells were found. FIG. 5 shows Blue Toluidine staining for acid components (mainly HA fibers-big spots, and cell nuclei-small dots) included in this coronal section of cells and scaffold 3 weeks after treatment. Host cell invasion filled the gaps between the fibers. Reabsorbing grey shades around some fibers testify the final step of host immune reaction to the scaffold. Scale bar is 50 µm.

However this reaction ended in time (>2 months). No significant difference in the biocompatibility of these matrices were found between the animals transplanted with scaffolds alone and those with scaffolds seeded with cells.

On the other hand, transplanted NSCs did not appear to be dramatically affected by this response.

Figure 6:
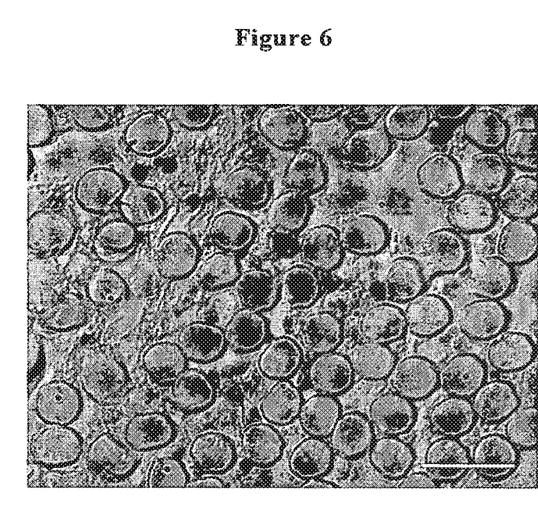
FIG. 6 shows nuclear staining of transgenic NSCs.

FIG. 6 shows nuclear staining of transplanted transgenic NSCs. Coronal section of the transplantation site: 20 days after surgery cells with nucleus marked in blue are adhering and branching between fibers of HA modified (empty black circle). Scale bar is 50 µm.

In this FIG. 6 it is possible to see a coronal section of the lesion site (approximately in the middle of the scaffold) 20 days after surgery: transplanted transgenic cells are marked in blue by means of the X-gal reaction, that marks the β-Galactosidase enzyme spontaneously produced by transplanted transgenic NSCs.

6 months after trauma, NSCs were also present in sections harvested caudally and rostrally to the lesion, thus showing an intrinsic capacity to migrate from the scaffold to the host tissue.

Most importantly, the regrowth of nervous tissue inside the lesions was tested by means of a routinely used technique to stain neurofilaments chemically (Bielshowsky silver staining for axons).

The treated animals presented an invasion of neuronal fibers from the area surrounding the lesion site: this effect could be seen no earlier than 1 month after transplantation.

Figure 7:
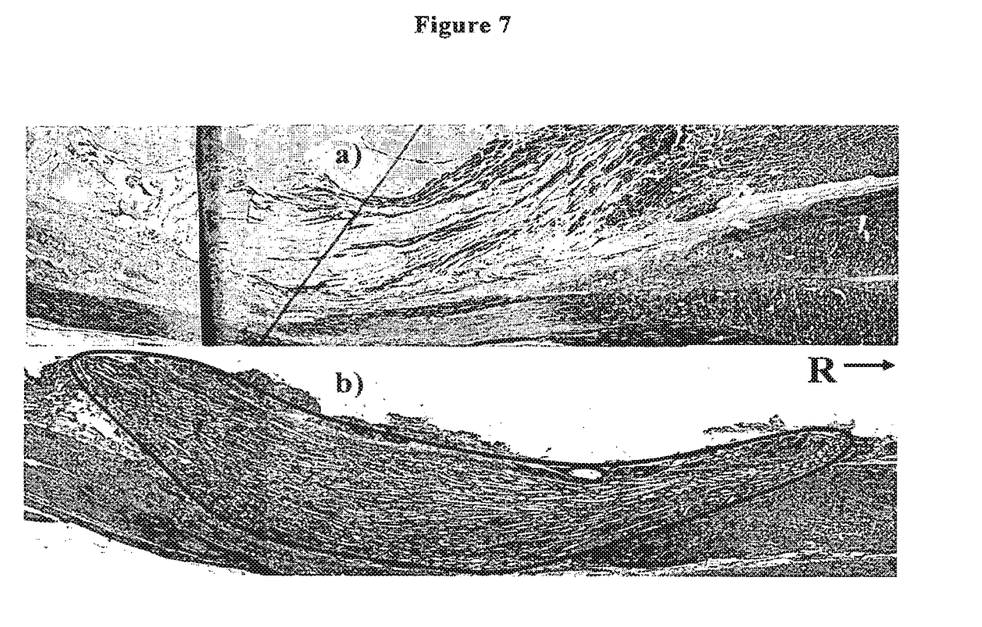
FIG. 7 shows neurofilament staining of a transversal section of spinal cord injury site fifty days after lesion.

FIG. 7 show neurofilament staining of transversal section of spinal cord injury site 50 days after lesion. Nervous fibers are stained in dark brown. Low (a) and high (b) magnification details of nervous regeneration in an animal transplanted with human NSCs and HYAFF®11 scaffold. (a) Round shapes left by the HA microfibers are still clearly visible, nervous fibers are invading the scaffold from the left (half-part left intact by surgery), the right portion of the image is still full of holes (=fibers). (b) High magnification image of regenerating neurons amongst HA microfibers. In some nervous bundles single fibers are visible.

Figure 8:
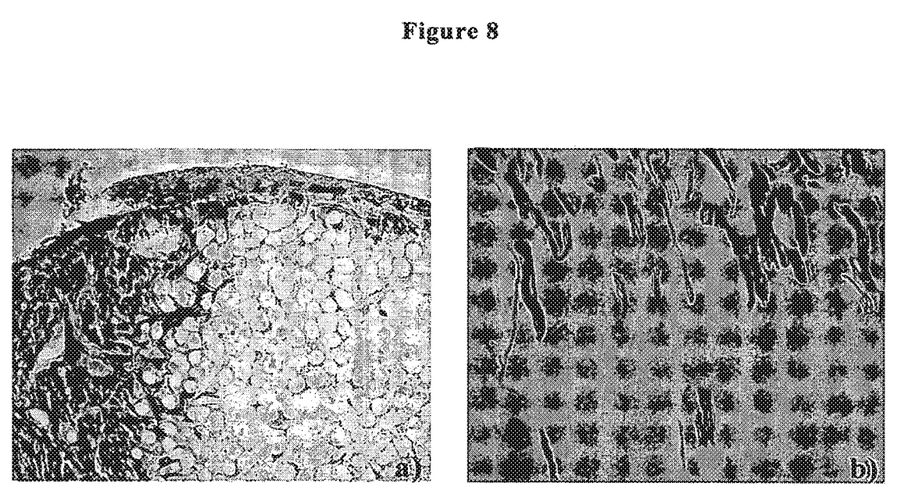
FIG. 8(a) shows neurofilament staining and FIG. 8(b) shows ematoxilin-eosin staining of consecutive longitudinal sections of injured and translated spinal cord.

FIG. 8 show (a) neurofilament and (b) haematoxilin-eosin stainings of consecutive longitudinal sections of injured and transplanted spinal cord. The animal was sacrificed 6 months after surgery. "R" point to the rostral side of the spinal cord. The transplantation site is encircled in the morphologic staining (b) by the red curve. Black line in (a) are artefacts due to the silver staining protocol used. Nervous fibers (dark brown lines) invaded the injury site from the rostral side.

Nervous fibers invaded the scaffold both laterally (figure 1ab) and rostrally (FIG. 8a) to the lesion site.

Particularly, it was possible to see regenerating nervous fiber extending processes significantly along the longitudinal spinal cord axis (FIG. 8a), providing support to the idea of using oriented microfibers to orient nervous regeneration.

In FIG. 8b, making use of a morphology immuno-histochemical staining (Haematoxilin-Eosin reaction) we colored cytoplasms and cell nuclei. The lesion site is artificially bordered by the red curve. To note, tissue parallel cavities are left by scaffold fibers, effect due to the long biodegradation time of 100% esterified HA when implanted in CNS tissues.

Figure 9:
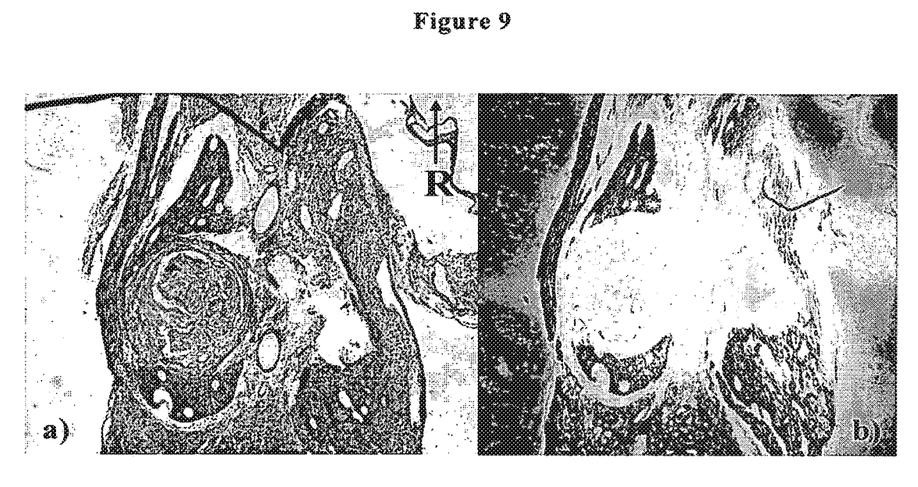
FIG. 9(a) shows ematoxilin-eosin staining and FIG. 9(b) shows neurofilament staingin of consecutive longitudinal sections of injured and transplanted spinal cord.

To date, all the scaffolds, whether seeded or not with NSCs, prevented the formation of aqueous cysts and glial scarring in all of the animal tested: the outcome that was found in the injured-only animals. FIG. 9ab show (a)

Haematoxylin-eosin and (b) neurofilament stainings of consecutive longitudinal sections of injured spinal cord (control group). The animal was sacrificed 6 months after surgery. "R" points to the rostral side of the spinal cord. Left picture shows huge massive tissue disruption, with a round shaped cyst completely free from nervous fibers (b). The continuous lines are present in both pictures as artefacts of the protocols used.

We also practiced the peripheral nerve transection (sciatic nerve) protocol (see previous paragraph) on 9 animals, adopting the previous strategy of 3-animal groups (scaffolds seeded with cells, scaffolds alone, nerves transected and not treated). Only in the injury sites of transplanted animals nervous fiber invasion, remyelination of regenerated fibers and revascularization were noticed (FIG. 10) 6 months after surgery.

Figure 10:
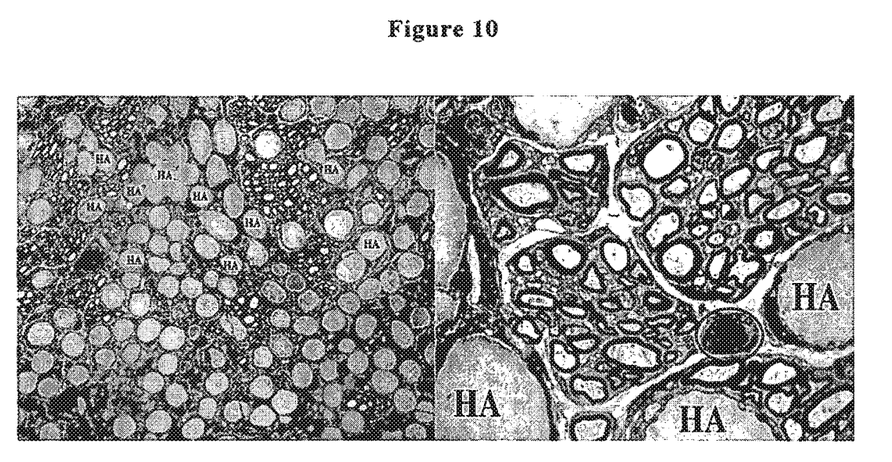
FIG. 10 shows Toluidine blue reaction of a transversal section of sciatic nerve transacted and transplanted with 100% estefified HA scaffold seeded with human NSCs.

In particular, FIG. 10 shows Toluidine blue reaction of transversal section of sciatic nerve transected and transplanted with 100% esterified HA scaffold seeded with human NSCs. Same section imaged at low (a) and high (b) magnification 6 months after lesion. Scaffold fibers are still present (HA marked circles) and between them a large amount of regenerated nervous fibers (a). Single nervous fibers are small dark-bordered circles in (b). The thicker the fiber sheet, the more remyelinated is. A blood vessel too is encircled by the red oval in (b).

We can assume that all the nervous fibers found between the scaffold fibers are regenerated fibers due to the complete section model we used for sciatic nerve transection.

Therefore, our results are the following:
- the biomaterial chosen was well tolerated by central and peripheral nervous systems: no persistent chronic immune response or cell apoptosis;
- nervous regeneration occurred amongst HA fibers in SCI and PNT models;
- the projected scaffold spatially influenced the spontaneous regeneration of nervous fibers;
- in the PNT model, nervous fibers were partially myelinated;
- NSCs survived 6 months after transplantation and migrated outside the lesion site.

The invention claimed is:

1. A method of regenerating nervous fibers in spinal cord or in peripheral nerve injury, said method comprising:
   a) preparing a three-dimensional parallel non-woven fiber scaffold comprising a biodegradable hyaluronic acid ester, wherein the scaffold fibers are spatially-oriented along the longitudinal axes of regenerating nervous fibers;
   b) submerging said scaffold into a coating solution capable of promoting Adult Neuronal Stem Cells adhesion, branching, proliferation and differentiation;
   c) contacting said coated scaffold obtained from step b) with Adult Neuronal Stem Cells, wherein Adult Neuronal Stem Cells are adhered onto said coated scaffold; and
   d) culturing and expanding adhered cells in the presence of growth or neurotrophic factors selected from bFGF (basic fibroblast growth factor), CNTF (ciliary neurotrophic factor), BDNF (brain derived neurotrophic factor) and GDNF (glial derived neurotrophic factor) or mixtures thereof for 2 days in vitro before the implantation;
   e) preparing the implant site;
   f) implanting the cell scaffold obtained from steps a-d) at the injury site prepared in step e);
   g) covering the implanted cell scaffold with a lamina or a tube to isolate the regeneration site from the surrounding tissues;
   h) suturing or sealing the implanted cell scaffold to the host tissue with fibrin glue, wherein said cell scaffold promotes the regeneration of said nervous fibers in spinal cord or in peripheral nerve injury.

2. The method according to claim 1, wherein said hyaluronic acid ester is a benzyl ester.

3. The method according to claim 2, wherein the hyaluronic acid ester has an esterification degree ranging between about 75% and 100%.

4. The method according to claim 1, wherein said coating solution comprises laminin or fibronectin, or laminin and fibronectin.

5. The method according to claim 4, wherein the laminin concentration is about 25 μg/ml.

6. The method according to claim 4, wherein the fibronectin concentration is about 50 μg/ml.

7. The method according to claim 1, wherein said Adult Neuronal Stem Cells are used in a range from about 9500 to 35000 cells/cm$^3$.

8. The method according to claim 1, wherein said growth or neurotrophic factors are used preferably with a concentration of about 20 ng/ml.

9. The method according to claim 1, wherein said scaffold fibers are in form of non-woven meshes and fibers, and woven tubular structures having porous structures.

10. The method according to claim 9, wherein said scaffold fibers have a diameter ranging from about 20 to 50 μm.

11. The method according to claim 1, wherein said lamina is square.

12. The method according to claim 1, wherein said cell scaffold is inserted into tubes made of esterified hyaluronic acid.

13. The method according to claim 12, wherein said tube is sutured with the device to both nerve stubs of the host tissue.

14. A method of manufacturing a cell scaffold comprising:
   a) preparing a three-dimensional parallel non-woven fiber scaffold comprising a biodegradable hyaluronic acid ester, wherein the scaffold fibers are spatially-oriented along the longitudinal axes of regenerating nervous fibers;
   b) submerging said scaffold into a coating solution capable of promoting Adult Neuronal Stem Cells adhesion, branching, proliferation and differentiation;
   c) contacting said coated scaffold obtained from step b) with Adult Neuronal Stem Cells, wherein Adult Neuronal Stem Cells are adhered onto said coated scaffold; and
   d) culturing and expanding adhered cells in the presence of growth or neurotrophic factors selected from bFGF (basic fibroblast growth factor), CNTF (ciliary neurotrophic factor), BDNF (brain derived neurotrophic factor) and GDNF (glial derived neurotrophic factor) or mixtures thereof; and
   e) obtaining said cell scaffold.

* * * * *

UNITED STATES PATENT AND TRADEMARK OFFICE
CERTIFICATE OF CORRECTION

| | |
|---|---|
| PATENT NO. | : 10,702,628 B2 |
| APPLICATION NO. | : 15/668716 |
| DATED | : July 7, 2020 |
| INVENTOR(S) | : Alessandra Pavesio et al. |

Page 1 of 3

It is certified that error appears in the above-identified patent and that said Letters Patent is hereby corrected as shown below:

In the Drawings

Please delete figure drawings 7 and 8 and insert replacement sheet figure drawings 7 and 8 attached hereto.

Signed and Sealed this
Twenty-fifth Day of August, 2020

Andrei Iancu
*Director of the United States Patent and Trademark Office*

Figure 7

Figure 8